US009539186B2

(12) United States Patent
Duffy et al.

(10) Patent No.: US 9,539,186 B2
(45) Date of Patent: *Jan. 10, 2017

(54) PERSONALIZING SUBSTANCE FOR APPLICATION TO THE SKIN OR ADDITION TO TATTOO INK AND METHODS OF PREPARATION THEREOF

(71) Applicant: Chamber Works, LLC, Wilmington, DE (US)

(72) Inventors: Patrick Duffy, Kennett Square, PA (US); Ellen Dias Jorgensen, South Salem, NY (US); Erich Boger, Kensington, MD (US); Edith Mathiowitz, Brookline, MA (US)

(73) Assignee: Chamber Works, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/016,864

(22) Filed: Feb. 5, 2016

(65) Prior Publication Data

US 2016/0158119 A1    Jun. 9, 2016

Related U.S. Application Data

(62) Division of application No. 14/593,409, filed on Jan. 9, 2015.

(60) Provisional application No. 61/925,827, filed on Jan. 10, 2014.

(51) Int. Cl.
| | | |
|---|---|---|
| *A61K 8/11* | (2006.01) | |
| *A61K 8/60* | (2006.01) | |
| *A61K 8/81* | (2006.01) | |
| *A61Q 1/02* | (2006.01) | |
| *A61K 8/02* | (2006.01) | |

(52) U.S. Cl.
CPC .............. *A61K 8/11* (2013.01); *A61K 8/0283* (2013.01); *A61K 8/606* (2013.01); *A61K 8/8135* (2013.01); *A61K 8/8141* (2013.01); *A61K 8/8147* (2013.01); *A61K 8/8152* (2013.01); *A61Q 1/025* (2013.01); *A61K 2800/30* (2013.01); *A61K 2800/412* (2013.01); *A61K 2800/43* (2013.01); *A61K 2800/591* (2013.01); *A61K 2800/652* (2013.01); *A61K 2800/91* (2013.01)

(58) Field of Classification Search
CPC ........ A61K 8/11; A61K 8/606; A61K 8/8152; A61K 8/8147; A61K 8/0283; A61K 2800/91; A61K 2800/412; A61K 2800/30; A61K 8/8141; A61K 8/8135; A61K 2800/652; A61K 2800/591; A61K 2800/43; A61Q 1/025
See application file for complete search history.

(56) References Cited

U.S. PATENT DOCUMENTS

| | | | |
|---|---|---|---|
| 3,266,987 A | | 8/1966 | Crowley et al. |
| 4,460,563 A | | 7/1984 | Calanchi |
| 4,794,000 A | | 12/1988 | Ecanow |
| 4,861,627 A | | 8/1989 | Mathiowitz et al. |
| 4,989,734 A | | 2/1991 | Mode et al. |
| 6,013,122 A | * | 1/2000 | Klitzman ................. A61K 8/14 106/31.03 |
| 6,262,034 B1 | | 7/2001 | Mathiowitz et al. |
| 6,461,571 B1 | * | 10/2002 | Tuffet .................... C12N 15/10 422/243 |
| 6,620,617 B2 | | 9/2003 | Mathiowitz et al. |
| 2002/0182258 A1 | | 12/2002 | Lunsford et al. |
| 2006/0159769 A1 | | 7/2006 | Lotan et al. |
| 2007/0072197 A1 | | 3/2007 | Rayms-Keller et al. |
| 2007/0184094 A1 | | 8/2007 | Williams |
| 2008/0167674 A1 | | 7/2008 | Bodduluri et al. |
| 2009/0217840 A1 | | 9/2009 | Kundakovic et al. |
| 2009/0311295 A1 | | 12/2009 | Mathiowitz et al. |
| 2012/0042882 A1 | | 2/2012 | Morales |
| 2012/0288537 A1 | * | 11/2012 | Schwendeman . A61K 47/48015 424/400 |
| 2015/0030545 A1 | | 1/2015 | Grass et al. |

FOREIGN PATENT DOCUMENTS

| | | |
|---|---|---|
| CN | 1161829 | 10/1997 |
| CN | 101768387 | 7/2010 |

(Continued)

OTHER PUBLICATIONS

Coyle, "What's in Your Microcapsule? Tattoo Ink—and More" https://news.brown.edu/articles/2007/07/microcapsule, Jul. 9, 2007.
Edmiston, "Leaving a Mark: How Ash Tattoos Help the Living Remember the Dead", National Post, Oct. 25, 2013.
Kladekova et al., "Preparation and Compaction Behavior of Poly(methyl methacrylate) Coated Iron Microparticles", J. Mater. Sci. Technol., 2010, vol. 26, No. 5, pp. 454-460.

(Continued)

*Primary Examiner* — Suzanne Ziska
(74) *Attorney, Agent, or Firm* — McCarter & English, LLP

(57) ABSTRACT

Compositions for delivering materials, such as a biological material, sand, soil, metal, water, sea water, holy water, synthetic or biological polymers, cremated ash, ceramics, animal or plant tissue, or another physiologically compatible component having personal significance to an individual are described herein. The material(s) are encapsulated in an inert, non-bioerodible, hydrophobic, polymeric material. Methods of making microparticles encapsulating the personalizing substance and methods of use are also provided. The personalizing substance may be encapsulated in a polymeric non-bioerodible microparticle. The encapsulated personalizing substance may be combined with a carrier for delivery to an individual's skin. In some embodiments, the personalizing substance is added to a tattoo ink and incorporated in a tattoo created on an individual's skin. Following injection in the skin, the encapsulated material remains in the microparticles, and is not released over time.

16 Claims, 2 Drawing Sheets

(56) References Cited

FOREIGN PATENT DOCUMENTS

| DE | 102008063246 | 7/2010 |
|---|---|---|
| EP | 1413206 | 4/2004 |
| GB | 929401 | 6/1963 |
| GB | 929406 | 6/1963 |
| JP | 2005307216 | 11/2005 |
| JP | 2006169161 | 6/2006 |
| JP | 2006290950 | 10/2006 |
| JP | 2007191503 | 8/2007 |
| JP | 2008162219 | 7/2008 |
| WO | WO-2005/046620 | 5/2005 |
| WO | WO-2008/054874 | 5/2008 |
| WO | WO-2009/079546 | 6/2009 |
| WO | WO-2012/136734 | 10/2012 |

OTHER PUBLICATIONS

Lin et al., "Synthesis and Characterisation of Polymethylmethacrylate/nanosilica and nanosilica/polymethylmethacrylate core-shell structure composite microsperes", Micro & Nano Letters, 2013, vol. 8, Iss. 5, pp. 217-220.

Mathiowitz et al., "Microencapsulation", Encyclopedia of Controlled Drug Delivery, John Wiley & Sons, Inc., 1999, vol. 2, pp. 493-546.

Van De Berg, et al., "Sheilding the cationic charge of nanoparticle-formulated dermal DNA vaccines is essential for antigen expression and immunogenicity", Journal of Controlled Release, 2010, vol. 141, No. 2, pp. 234-240.

Von Wurmb-Schwark et al., "Genetic Investigation of Modern Burned Corpses", International Congress Series, 2004, vol. 1261, pp. 50-52.

Wang et al., "Polymer-Encapsulated Gold-Nanoparticle Dimers: Facile Preparation and Catalytical Application in Guided Growth of Dimeric ZnO-Nanowires", Nano Letters, 2008, vol. 8, No. 9, pp. 2643-2647.

"The Cremation Process", The American Cremation Directory, http://www.lowcostcremation.com/what_is_cremation.html, downloaded Jul. 22, 2015.

"Scanning Electron Microscope", Wikipedia, the free Encyclopedia, Retrieved Jan. 17, 2016, from https//en.wikipedia.org/wiki/Scanning_electron_microscope, pp. 1-19.

International Search Report and Written Opinion for International Application No. PCT/US2015/010822, mailed Apr. 8, 2015.

Anthony Sebastian, "Harvard Cracks DNA Storage, Crams 700 Terabytes of Data Into a Single Gram", Retrieved May 5, 2016, from http://www.extremetech.com/extreme/134672-harvard-cracks-dna-storage-crams-700-terab . . . , pp. 1-9.

International Preliminary Report on Patentability; International Application No. PCT/US2015/010822; mailed Jul. 12, 2016.

Oh et al., "Integrated Bio-Inorganic Hybrid Systems for Nano-Forensics", Chem. Soc. Rev., 2011, vol. 40, pp. 583-595.

* cited by examiner

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ttaactccac cattagcacc                                              20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gaggatggtg gtcaagggac                                              20
```

PERSONALIZING SUBSTANCE FOR APPLICATION TO THE SKIN OR ADDITION TO TATTOO INK AND METHODS OF PREPARATION THEREOF

CROSS-REFERENCE TO RELATED APPLICATIONS

This application is a Divisional of U.S. application Ser. No. 14/593,409, filed Jan. 9, 2015, which claims priority to U.S. Provisional Patent Application No. 61/925,827 filed on Jan. 10, 2014, the contents of each of which are incorporated herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 121608_00010_Sequence_Listing. The size of the text file is 1 KB, and the text file was created on Feb. 4, 2016.

FIELD OF THE INVENTION

The present invention relates to personalizing materials to be added to the skin, such as additives for tattoo ink.

BACKGROUND OF THE INVENTION

Humans have been applying tattoos to the skin for thousands of years. For example, the first recorded formula for mixing and applying tattoo ink dates back to the fifth century and is attributed to the Roman physician Aetius. Tattoo inks were derived from natural substances and comprised a suspension of pigmented particles in a liquid carrier. Applying tattoo ink with needles or similar instruments to the skin, where the ink remains permanently, produces tattoos. This technique introduces the pigment suspension through the skin by an alternating pressure-suction action caused by the elasticity of the skin in combination with the movement of the needle. Water and other carriers for the pigment introduced into the skin diffuse through the tissues and are absorbed. Once the skin has healed, most pigment particles remain in the interstitial space of the tissue. During the healing process, some particles of pigment are eliminated from the skin surface. After healing, the tattoo is made up of the remaining particles of pigment located in the dermis where they are engulfed by phagocytic skin cells or are retained in the extracellular matrix. See US Published application no. 2009/0311295 to Mathiowitz et al. Inks used for tattooing resist elimination due to their inertness and the relatively large size of the insoluble pigment particles. A tattoo produced in this manner will partially fade over time but will generally remain visible. Tattoos are used for a variety of reasons, primarily for ornamentation of the skin. See U.S. Pat. No. 6,013,122 to Klitzman & Koger.

Despite advances in methods of applying tattoo ink to the skin, such as the electric tattoo ink gun, tattoo inks in commercial use today are similar to those used centuries ago. Standard tattoo inks contain a pigment comprising metal salts dissolved in a carrier, usually ethanol or water, to disperse the pigment in the dermis. See U.S. Pat. No. 6,013,122. Thus a need exists for novel formulations of tattoo ink with improved properties.

SUMMARY OF THE INVENTION

Compositions for delivering materials, such as a biological material, sand, soil, metal, water, sea water, holy water, synthetic or biological polymers, cremated ash, ceramics, animal or plant tissue, or another physiologically compatible component having personal significance to an individual are described herein. These materials may be encapsulated and then administered to the skin of an individual to create a personalized tattoo.

The material(s) are encapsulated in a nonbioerodible, polymeric microparticle, wherein the microparticle comprises a biocompatible, non-bioerodible, hydrophobic polymer. Preferably the polymers (copolymers, or blends thereof) that form the microparticles have a glass transition temperature that is higher than 60° C. or have a melting point that is greater than 50° C. Methods of making and using the compositions are also provided.

A personalized ink tattoo creates a physical connection with a person, object, place, or event, because the personalized tattoo incorporates into the tattoo ink and, therefore, the image displayed in the skin, a personalizing substance. The compositions described herein may be delivered to a person's skin to create a personalized ink tattoo. For example, the compositions may be additives to a tattoo ink. Alternatively, the compositions can be delivered to the individual's skin without adding a tattoo ink, for example, by administering the composition to a site where a tattoo is already present.

The composition is delivered to the individual in a suitable carrier, optionally in combination with a tattoo ink. For example, at the time of use, the composition may be mixed with the tattoo ink and the mixture can be applied using a standard tattoo needle and procedure.

Alternatively, the composition is administered with a suitable carrier to one or more desired sites in an individual's skin. Typically, a marker is added to the site, or the site contains a marker, to indicate the location of the encapsulated material.

Following delivery to an individual's skin, the encapsulated material remains in the microparticles and the microparticles do not erode. The encapsulated material is not released from the microparticles. The encapsulated material remains in the microparticles for as long as it is in the individual's body, such as for at least 5 years, at least 10 years, at least 15 years, at least 20 years, or for a longer period of time.

In a preferred embodiment, the composition includes DNA obtained from one or more humans, non-human animals, or plants of significance to the individual, or any combination thereof. The DNA may be obtained by any standard method, such as a non-invasive cheek-swab. The DNA is encapsulated in a non-bioerodible, polymeric microparticle, wherein the microparticle comprises a biocompatible, hydrophobic, non-bioerodible polymer.

In some aspects, the invention relates to a composition comprising a personalizing substance encapsulated in a non-bioerodible, polymeric microparticle, wherein the microparticle comprises a biocompatible, hydrophobic, non-bioerodible polymer, and wherein the microparticle does not release the personalizing substance. In certain embodiments, the composition further comprises a carrier suitable for injection into the skin. In certain embodiments, the personalizing substance is in the form of nanoparticles. In certain embodiments, the personalizing substance is selected from the group consisting of DNA, sand, soil, metal, cremated ash, ceramics, and plant tissue. In certain embodiments, the personalizing substance is DNA and wherein the DNA further comprises a personal identification characteristic selected from the group consisting of short tandem repeats (STRs), single nucleotide polymorphisms (SNPs), epigenetic markers, and methylated DNA patterns. In a particular embodiment, the personalizing substance is cremated ash.

In certain embodiments of the compositions described herein, the polymer is selected from the group consisting of polyvinyl acetate, polyacrylate, polymethacrylate, and copolymers and blends thereof. In certain embodiments the polymer has a glass transition temperature that is greater than or equal to 60° C. or has a melting point greater than or equal to 50° C.

In certain embodiments of the compositions described herein, the personalizing substance is DNA, and wherein the microparticles comprise up to 0.01% (w/w) DNA. In certain embodiments, the personalizing substance is not DNA, and wherein the microparticles comprise up to 10% (w/w) of the personalizing substance.

In certain embodiments, the composition further comprises a tattoo ink, wherein the ink comprises at least one pigment or dye.

In some aspects, the invention relates to a method of encapsulating a personalizing substance for administering to the skin of an individual, comprising: (a) isolating the personalizing substance from a source organism or source material; and (b) encapsulating the personalizing substance in a non-bioerodible, polymeric microparticle, wherein the microparticle comprises a biocompatible, hydrophobic, non-bioerodible polymer, and wherein the microparticle does not release the personalizing substance. In certain embodiments, the method further comprises micronizing the personalizing substance before step (b). In certain embodiments, the method further comprises forming the personalizing substance into a nanoparticle before step (b). In certain embodiment, the personalizing substance is DNA. In certain embodiments, the method further comprises amplifying the DNA prior to step (b). In some embodiments, the DNA is in liquid form prior to step (b). In some embodiments, the DNA is human DNA.

In certain embodiments of the method described above, step (b) comprises forming the microparticles by a process selected from the group consisting of solvent evaporation microencapsulation, double wall formation of microspheres by solvent evaporation, hot melt encapsulation, phase separation encapsulation, spontaneous emulsion, solvent removal microencapsulation, and coacervation. In certain embodiments, a single batch of the composition is formed comprising dry microparticles, wherein the mass of the batch of dry microparticles ranges from approximately 1 g to 3 g.

In certain embodiment, the method described above further comprises: (c) analyzing the personalizing substance isolated from the source organism or source material; (d) analyzing the personalizing substance encapsulated in the microparticle; and (e) comparing data obtained in step (d) to data obtained in step (c) to confirm that the personalizing substance isolated from the source organism or source material is the same as the personalizing substance encapsulated in the microparticle.

In some aspects, the invention relates to a method of delivering a personalizing substance to the skin of an individual comprising injecting into the individual's skin a composition comprising non-bioerodible microparticles, wherein the microparticles comprises a biocompatible, hydrophobic, non-bioerodible polymer and encapsulated personalizing substance, and wherein the microparticle does not release the personalizing substance. In certain embodiments, the injection is made at the site of an existing tattoo. In certain embodiments, the method further comprises mixing the microparticles with a tattoo ink prior to injection. In certain embodiments, the step of injecting is repeated multiple times at different sites on the skin to form a tattoo design. In certain embodiments, the personalizing substance is in the form of nanoparticles. In certain embodiments, the personalizing substance is selected from the group consisting of DNA, sand, soil, metal, cremated ash, ceramics, and plant tissue. In certain embodiments, the microparticles have a size ranging from 1 micron to 5 microns.

In certain embodiments of the method described above, the personalizing substance is DNA and wherein the DNA further comprises a personal identification characteristic selected from the group consisting of short tandem repeats (STRs), single nucleotide polymorphisms (SNPs), epigenetic markers, and methylated DNA patterns.

In certain embodiments of the method described above, the polymer has a glass transition temperature that is greater than or equal to 60° C. or has a melting point greater than or equal to 50° C.

DETAILED DESCRIPTION OF THE INVENTION

I. Definitions

Figure 1:
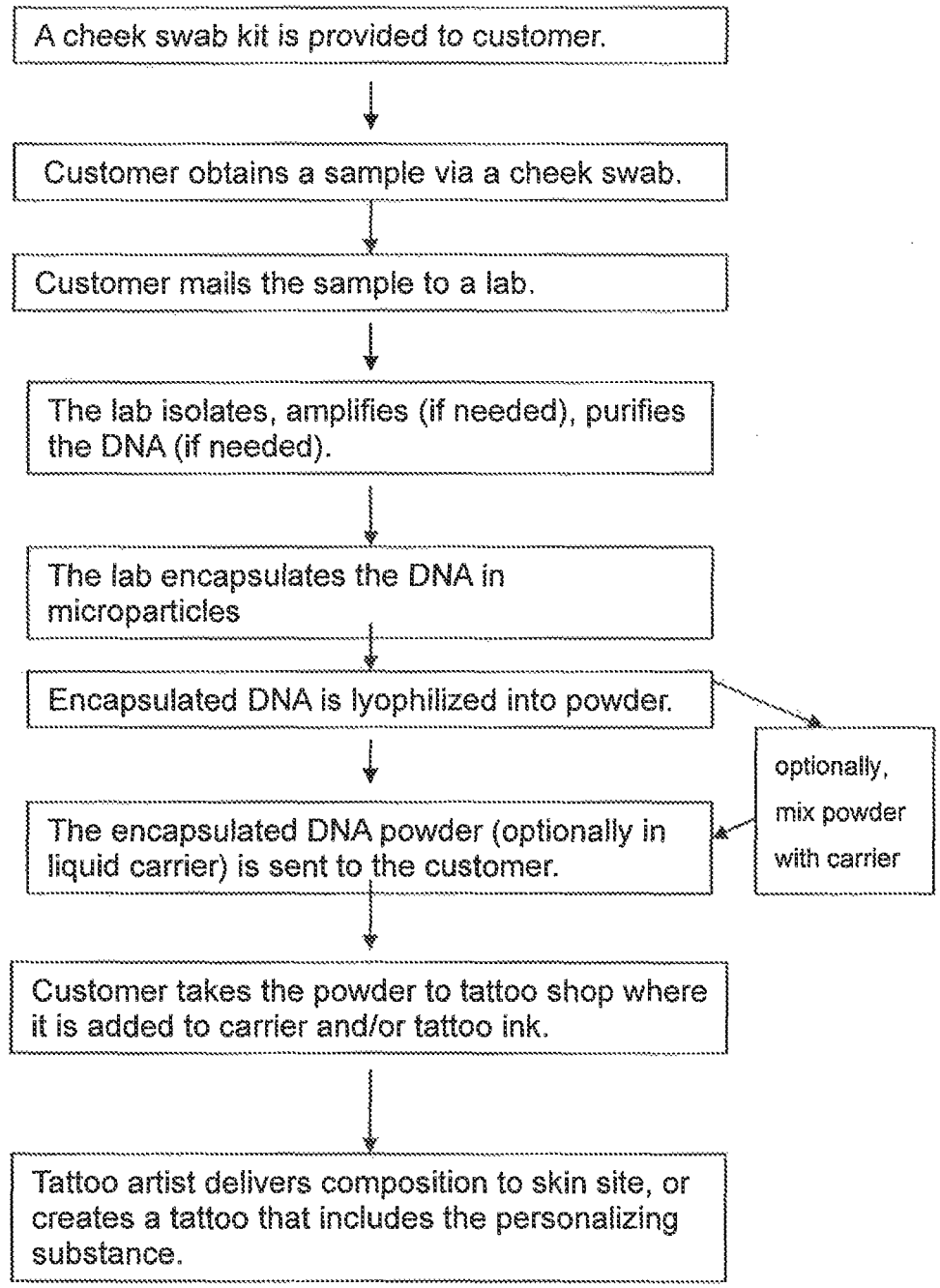
FIG. 1 is a flow chart showing the steps of an exemplary end-to-end process for delivering to a customer a tattoo that incorporates DNA of personal significance. The steps performed by the customer and then by the lab generate encapsulated DNA, alone (dry powder), or in liquid form (e.g. with a carrier solution), which is added as an additive to a tattoo ink.

As used herein, the term "personalizing substance" refers to a material of significance to an individual. The personalizing substance may be a natural or synthetic material, where at least a portion of the material is capable of being encapsulated in a polymeric microparticle. The term personalizing substance is used herein to refer to the material both prior to and subsequent to encapsulation.

The terms "additive" and "additive composition" are used interchangeably herein to refer to a composition that is added to an existing tattoo or to a tattoo ink, with or without a carrier, prior to or during, tattooing.

The terms "non-bioerodible" and "non-erodible" as used herein mean inert or unreactive under physiological conditions in the skin. The non-bioerodible polymers and the resulting polymeric microparticles described herein are able to withstand physical dissolution and/or chemical degradation processes under the physiological environment of biological tissues, particularly the skin, typically for at least 5 years, at least 10 years, at least 15 years, at least 20 years, or even longer following application to an individual's skin, such as via injection into the skin.

As used herein, the term "hydrophobic polymer" refers to polymers that have a low affinity for water (at physiological temperature, e.g. 37° C.) and have a lower solubility in water than polylactic acid (PLA).

As used herein, the term "high molecular weight" means a molecular weight above 10,000 Daltons (Da), preferably above 20,000 Da.

As used herein, the terms "carrier" or "additive carrier" mean a composition for dissolving or storing a personalizing substance in encapsulated form. The carrier is typically suitable for injection into the human skin.

As used herein, the term "encapsulated material," means the molecular components of the personalizing substance. For example, if the personalizing substance is sand, then the encapsulated material includes silica ($SiO_2$), calcium silicate ($Ca_2SiO_4$), calcium nitride ($CaN_2$), and/or silicon nitride ($Si_3N_4$), etc.

As used herein, the term "biological material" means any biological substance, including, but not limited to biological micromolecules, such as a nucleotides, amino acids, cofactors, or hormones, biological macromolecules, such as nucleic acids, polypeptides, proteins (for example enzymes, receptors, secretory proteins, structural and signaling proteins, hormones, ligands, etc.), polysaccharides, and/or any combination thereof.

As used herein, the term "physiologically compatible component" means any component in a composition that is compatible with the physiology of the recipient, typically a human.

As used herein, the term "recipient" refers to the recipient of the encapsulated personalizing substance. The recipient may be any subject, human, animal or plant, capable of receiving the encapsulated personalizing substance.

As used herein, "nanoparticle" refers to a particle or a structure in the nanometer (nm) range, typically from about 1 to about 1000 nm in diameter.

As used herein, a "microparticle" is a particle of a relatively small size, but not necessarily in the micron size range; the term is used in reference to particles of sizes that can be, for example 1 to about 1000 microns. The term "microparticle" encompasses microspheres, microcapsules and microparticles, unless specified otherwise. A microparticle may be of composite construction and is not necessarily a pure substance; it may be spherical or any other shape.

As used herein, the term "percent loading" refers to a ratio of the weight of a personalizing substance to the weight of a microparticle, multiplied by 100.

As used herein, the term "small batch" refers to a batch size of an encapsulated personalizing substance suitable for use by no more than one, no more than two, no more than three, no more than four, no more than five, no more than six, no more than seven, no more than eight, no more than nine, or no more than ten individuals, optionally with a small amount remaining after application to the individual for verification purposes. In some embodiments, the batch size of the encapsulated personalizing substance is less than about 10,000, 5000, 4000, 3000, 2000, 1000, 500, 100, 50, 10, 1, 0.1 or 0.01 mg. Any of these values may be used to define a range for the batch size of the encapsulated personalizing substance. For example the batch size of the encapsulated personalizing substance may range from about 10,000 mg to about 0.01 mg, from about 10,000 mg to about 1000 mg, or from about 5000 mg to about 500 mg.

II. Compositions

Compositions for placing a personalizing substance in the skin of an individual, to remain at the site of placement, are described herein. The personalizing substance is encapsulated in the microparticles and is also referred to herein as "the encapsulated material". The compositions may be used to personalize tattoos and/or integrate substances of special significance to an individual into his/her skin.

Following delivery to an individual's skin, the encapsulated material remains in the microparticles, and the microparticles do not erode. The encapsulated material is not released from the microparticles. A simple in vitro test can be used to confirm that the microparticles will not release the encapsulated material following delivery to an individual's skin. For example, after formation of microparticles containing an encapsulated personalizing substance, the microparticles can be immersed in aqueous solution or buffer at pH 7.4 and temperature of 37° C. in a bath for at least about 1 month. Samples are removed periodically, such as after 1 hour, after 1 day, after 1 week, and after 1 month and analyzed using a suitable detection method to determine if any traces of the encapsulated material are in the aqueous solution, buffer, or supernatant.

Suitable detection methods are known in the art. For example, suitable methods for detection of whether any DNA is released include detection of the fluorescence of labeled DNA released into the aqueous solution, buffer, or supernatant and/or PCR amplification of the aqueous solution, buffer, or supernatant. PCR methods for detecting low levels of DNA in a sample are known in the art. See, for example, Sambrook, et al., Molecular Cloning. (4th ed.). Cold Spring Harbor, N.Y.: Cold Spring Harbor Laboratory. Conventional PCR and real-time PCR with real-time monitoring of amplification may be used to detect any DNA release. The PCR amplification may use the same primers and amplification conditions as those used for amplification of DNA prior to encapsulation. The PCR amplification may follow up to 50 amplification cycles and generates a detectable number of amplified DNA molecules, if any DNA is present in the aqueous solution, buffer, or supernatant, referred to as "the amplified product"). Following PCR, the amplified product, if present, may be detected by conventional gel electrophoresis techniques or UV-Vis spectrometry for detecting double-stranded DNA. See, for example, Sambrook, et al., Molecular Cloning. (4th ed.). Cold Spring Harbor, N.Y.: Cold Spring Harbor Laboratory. Presence of an amplified product following the process described above indicates release of DNA from the microparticles, and absence of amplified product indicates that DNA was not released from the microparticles For non-DNA personalizing substances, suitable detection methods include, IR, mass spectrometry, for example, isotope-ratio mass spectrometry (IRMS) or liquid chromatography mass spectrometry (LC-MS).

As used herein the term "a microparticle that does not release the personalizing substance" refers to a microparticle that does not release a substantial amount of the personalizing substance in the aqueous solution or buffer as detected by an in vitro assay as described above. In some embodiments, the microparticle does not release a detectable amount of the personalizing substance after 1 hour, 1 day, 1 week, 2 weeks, 3 weeks, 1 month, 6 months, 1 year, 5 years, 10 years, 20 years, or 30 years as determined by an in vitro assay as described above. In some embodiments, the microparticle releases less than 10%, 5%, 1%, 0.5%, 0.1%, 0.05%, 0.01%, 0.005% or 0.001% of the total amount of the personalizing substance contained in the microparticle. In some embodiments, the microparticle releases less than 10%, 5%, 1%, 0.5%, 0.1%, 0.05%, 0.01%, 0.005% or 0.001% of the total amount of the personalizing substance contained in the microparticle after 1 hour, 1 day, 1 week, 2 weeks, 3 weeks, 1 month, 6 months, 1 year, 5 years, 10 years, 20 years, or 30 years. In a particular embodiment, the microparticle releases less than 0.1% of the total amount of the personalizing substance (e.g. DNA) contained in the microparticle after 2 weeks.

For compositions with DNA as the encapsulated personalizing substance, the detection method following an in vitro assay as described above includes amplification by PCR followed by detection by conventional gel electrophoresis techniques or UV-Vis spectrometry. For compositions with non-DNA material(s) as the encapsulated personalizing substance, mass spectrometry may be used as the detection method following an in vitro assay as described above.

1. Personalizing Substance

Generally, the compositions described herein include a personalizing substance. Suitable personalizing substances include, but are not limited to, biological materials such as, for example, animal or plant tissue, sand, soil, metal, sea water, holy water, synthetic or natural polymers, cremated ash, ceramics, and other physiologically compatible components. In the case of liquid personalizing substances such as sea water and holy water, lyophilization of microparticles comprising the personalizing substance would remove any liquid contained in the microparticle. However, any salts or other non-volatile compounds contained in the liquid would remain.

In some embodiments, the compositions may contain encapsulated DNA without any additional personalizing substances. In other embodiments, the compositions contain a personalizing substance comprising DNA and one or more additional personalizing substances comprising other compounds. For example, the additional personalizing substances may be one or more samples from sand, soil, metal, ceramics, and/or plant products.

A. Exemplary Personalizing Substances

Suitable personalizing substances include, but are not limited to, sand, soil or rock particles, or compounds extracted from sand, soil or rock.

Sand consists predominately of silica ($SiO_2$) and other organic and inorganic minerals, such as calcium silicate ($Ca_2SiO_4$), calcium nitride ($Ca_3N_2$), silicon nitride ($Si_3N_4$), aluminum nitride ($AlN_3$), alumina ($Al_2O_3$), borazone "boron nitride" (BN), magnesium oxide (MgO), silicon oxysulfide (SiOS), lithium silicate ($Li_2SiO_4$), as well as other metal oxides/nitrides, as shown in Table 1.

The identity of personalizing substances that do not contain DNA, such as sand, soil, metal, water, sea water, holy water, synthetic or natural polymers, cremated ash, ceramics, and compounds derived from plants, may be confirmed by a suitable method, such as mass spectrometry, for example, isotope-ratio mass spectrometry (IRMS) or liquid chromatography mass spectrometry (LC-MS).

TABLE 1

Exemplary Personalizing Substances

| Source for Personalizing Substance | Personalizing Substance |
|---|---|
| White Beach Sand | Quartz ($SiO_2$) particles of different diameter ranges and limestone from coral or shells. |
| Dark Sand | Quartz ($SiO_2$) particles of different diameter ranges and magnetite. |
| Green Sand | Quartz ($SiO_2$) particles of different diameter ranges and chlorite |
| Rock | Quartz ($SiO_2$) particles of different diameter ranges and other trace elements that vary with geographical location. |

For example, the personalizing substance may contain silicon dioxide particles extracted from a soil or rock sample. Suitable extraction techniques are known. Following extraction, the particles may be ground by conventional means to reduce their size to less than 1 micron, optionally the particles are then screened to obtain a population of particles having a size range for encapsulation, or micronized to produce nanoparticles of suitable size, typically from about 1 to about 1000 nm in diameter. Optionally, the particles may be mixed with powdered or pre-dispersed tattoo ink after encapsulation.

In some embodiments, the personalizing substance comprises particles of a metal or ceramic object having meaning to a person receiving the substance. For example, such metal or ceramic objects can be ground, screened and extracted to remove unwanted components, encapsulated, and mixed with tattoo ink for inclusion in a tattoo.

In some embodiments, the personalizing substance includes extracts of wooden items that have personal meaning to the individual. For example, in some embodiments cellulose is extracted from the wood item and encapsulated for delivery to the individual.

The personalizing substance may be added as a solid or in the form of a liquid, such as in the form of an emulsion, to the microparticle forming material. Following encapsulation, the personalizing substance is in the form of small particles, typically nanoparticles, in the microparticle. Generally, the personalizing substance is in the core of the microparticles and is surrounded by the hydrophobic, non-erodible polymeric matrix, i.e. the shell. The encapsulated personalizing substance has a size smaller than the resulting microparticles, and is typically smaller than 1 micron in diameter (or in its largest dimension for non-spherical particles).

B. Types of DNA Molecules in Personalizing Substances

The personalizing substances are intended to remain inert and unreactive and to remain encapsulated following delivery to the skin.

Accordingly, in some embodiments, the personalizing substance does not comprise a vector. As used herein the term "vector" refers to a DNA molecule used in biotechnology for storage, propagation, delivery or integration of recombinant DNA. Examples of vectors include plasmid backbones, viral vectors, bacmids, cosmids, and artificial chromosomes.

Generally, the vector itself is a DNA sequence that consists of an insert (transgene, or recombinant DNA) and a larger sequence that serves as the "backbone" of the vector. The purpose of a vector is to transfer the insert to another cell, where it may be isolated, multiplied, or expressed. In some embodiments, the personalizing substance does not comprise DNA that is used to transfer a DNA sequence into a cell. In some embodiments, the personalizing substance does not comprise DNA used for the purpose of multiplying or expressing the genetic information contained within it.

C. Optional Components

1. Personal Identification Characteristics

Optionally, the compositions include one or more personal identification characteristics. The one or more personal identification characteristics contain unique information which can be used to verify that the personalizing substance was obtained from a particular source, e.g., human, non-human animal, or plant. A verification step may be made prior to or subsequent to encapsulation, optionally verification may occur after the personalizing substance is placed in the skin of an individual.

Exemplary personal identification characteristics for DNA include, but are not limited to, microsatellite markers such as short tandem repeats (STRs) and Simple Sequence Repeat (SSR) markers, single nucleotide polymorphisms (SNPs), and epigenetic markers, such as methylated DNA patterns. Any DNA sequence that is unique to the source organism may be used as a personal identification characteristic. For example the DNA sequence unique to the source organism may be identified by sequencing the entire sequence of the DNA isolated from the source organism, or a portion thereof, using sequencing methods known in the art such as Sanger sequencing or next generation sequencing, e.g. Illumina sequencing. DNA sequencing methods are well known in the art and are described, for example, in Sambrook, et al., Molecular Cloning, (4th ed.). Cold Spring Harbor, N.Y.: Cold Spring Harbor Laboratory.

a. Polymorphic Genetic Markers

DNA generally includes one or more polymorphic genetic markers. Polymorphic genetic markers are highly variable regions of the genome which have contributed to the development of a variety of applications such as forensic DNA analysis and paternity testing that are used to unambiguously identify individuals.

The identification of many polymorphic genetic markers has occurred over the last thirty years. For example, polymorphic genetic markers known as variable number of tandem repeats (VNTRs) are abundant and highly polymorphic regions of DNA containing nearly identical sequences, 14 to 80 bases in length, repeated in tandem. See Jeffreys et al., 1985, Nature 314: 67-73; Wyman et al., 1980, PNAS 77: 6754-6758; and Nakamura et al., 1987, Science 235: 1616-1622. The variation in these markers between individuals makes them useful for identifying particular individuals. VNTRs may be detected from small amounts of DNA using polymerase chain reaction (PCR). See Kasai et al., 1990, Journal of Forensic Sciences 35(5): 1196-1200. Size differences in the amplified PCR products are detected on agarose or polyacrylamide gels. However, the finite number of VNTRs limits the widespread applicability of this method, which in turn led to the identification of short tandem repeats (STR).

b. Short Tandem Repeats (STR)

STRs can be amplified by a polymerase chain reaction, and are highly abundant and polymorphic (variable from individual to individual). STRs can contain tandem repeat sequences that differ by two (dinucleotide), three (trinucleotide), four (tetranucleotide) or five (pentanucleotide) base pairs. It is estimated that there are approximately 50,000 to 100,000 dinucleotide repeats in the human genome. Trinucleotide and tetranucleotide repeats are less common; the human genome is estimated to contain 10,000 of each type of repeat. See Tautz et al, 1989, Nuc. Acids Res. 17: 6464-6471; and Hamada et al., 1982, PNAS 79: 6465-6469. The use of tetranucleotide and pentanucleotide STRs allows better discrimination of differences between individual subjects relative to the shorter sequences. See Weber et al., 1989, Am J Hum Genet 44: 388-396.

The personalizing substance may contain a human DNA sequence selected from the group consisting of a dinucleotide STR, a trinucleotide STR, a tetranucleotide STR and a pentanucleotide STR.

Because the size of PCR products from human tetranucleotide repeat regions typically varies between individuals, tetranucleotide repeats are a preferred personal identification molecule for use as a personalizing substance. For example, PCR products of two different sizes are observed based on the inheritance for each individual of one copy of the polymorphic marker from each parent. Each inherited copy contains a variable number of tetranucleotide repeats. Thus, two unrelated individuals likely will produce different sized PCR products from the same tetranucleotide polymorphic marker. As a greater number of different tetranucleotide repeat regions are compared between individuals, the probability of those individuals sharing the identical pattern of PCR products decreases.

c. Single Nucleotide Polymorphisms (SNPs)

Single nucleotide polymorphism is a DNA sequence variation occurring commonly within a population (e.g. 1%) in which a single nucleotide—A, T, C or G—in the genome (or other shared sequence) differs between members of a biological species or paired chromosomes. For example, two sequenced DNA fragments from different individuals, AAGC<u>C</u>TA to AAGC<u>T</u>TA, contain a difference in a single nucleotide.

SNPs may fall within coding sequences of genes, non-coding regions of genes, or in the intergenic regions (regions between genes). SNPs within a coding sequence do not necessarily change the amino acid sequence of the protein that is produced, due to degeneracy of the genetic code.

SNPs in the coding region are of two types, synonymous and nonsynonymous SNPs. Synonymous SNPs do not affect the protein sequence while nonsynonymous SNPs change the amino acid sequence of protein. The nonsynonymous SNPs are of two types: missense and nonsense.

SNPs that are not in protein-coding regions may still affect gene splicing, transcription factor binding, messenger RNA degradation, or the sequence of non-coding RNA. Gene expression affected by this type of SNP is referred to as an eSNP (expression SNP) and may be upstream or downstream from the gene.

SNPs without an observable impact on the phenotype (so called silent mutations) are still useful as genetic markers in genome-wide association studies, because of their quantity and the stable inheritance over generations.

2. Nanoparticles

Optionally, the personalizing substance(s) are formed into or encapsulated in nanoparticles prior to encapsulation in the polymeric microparticles.

Any of the aforementioned personalizing substances may be micronized to produce nanoparticles of suitable size.

In some embodiments the nanoparticle comprises or consists of DNA from a human or from a companion animal. The DNA may be precipitated by calcium phosphate. In other embodiments, the nanoparticle comprises, consists of, or is derived from non-DNA personalizing substance, such as sand, soil, metal, water, sea water, holy water, synthetic or biological polymers, cremated ash, or ceramics. In certain embodiments the nanoparticles are formed by micronizing the personalizing substance to reduce its size, in preparation for microencapsulation.

The diameter of the nanoparticle may be, for example, about 1000, 900, 800, 700, 600, 500, 400, 300, 200, 100, 90, 80, 70, 60, 50, 40, 30 or 20 nanometers (nm). In certain embodiments, the diameter of the nanoparticle is less than about 1000, 900, 800, 700, 600, 500, 400, 300, 200, 100, 90, 80, 70, 60, 50, 40, or 30 nanometers (nm). Any of these values may be used to define a range for the diameter of the nanoparticle. For example, the diameter of the nanoparticle may be from about 20 nm to about 1000 nm or from about 20 nm to about 100 nm.

2. Polymeric Microparticles

The personalizing substance is encapsulated in a polymeric microparticle. The core of the microparticles contains the personalizing substance, which is surrounded by a polymeric matrix that forms the outer shell of the microparticles.

Optionally, the personalizing substance is formed into nanoparticles, which are encapsulated in the polymeric microparticle. In some embodiments, the personalizing substance is a DNA nanoparticle which is prepared by calcium phosphate precipitation. The calcium phosphate precipitated DNA nanoparticle may be encapsulated in a polymeric microparticle without dissolving the DNA in a solvent.

In some embodiments, the microparticle comprises both a personalizing substance and a pigment or dye. Pigment or dye particles in the polymeric microparticles are generally smaller than 100 nm and preferably smaller than 20 nm. In some embodiments, the microparticle comprising the personalizing substance does not include a pigment or dye.

A. Polymers

Any polymer that is hydrophobic, biocompatible, and non-bioerodible may be used to form the microparticles. Preferably the composition and molecular weight of the polymers that form the microparticles are such that the glass transition temperature of the polymers is greater than or equal to 60° C. or the melting point of the polymers is greater than or equal to 50° C. In certain embodiments, the glass transition temperature of the polymers is greater than or equal to about 60, 61, 62, 63, 64, 65, 66, 67, 68, 69, 70, 75, or 80° C. In certain embodiments, the melting point of the polymers is greater than or equal to about 50, 51, 52, 53, 54, 55, 56, 57, 58, 59, 60, 65 or 70° C. Preferred polymers with a high glass transition temperature, i.e. a glass transition temperature that is greater than or equal to 60° C., or high melting point, i.e. a melting point that is greater than or equal to 50° C., include, but are not limited to, poly(methyl methacrylate) (PMMA), polystyrene, polyethylene terephthalate, and polycarbonate. In a particular embodiment, the polymer is selected from the group consisting of polyvinyl acetate, polyacrylates, polymethacrylates, and copolymers and blends thereof. In another particular embodiment, the polymer is selected from the group consisting of polyacrylates, polymethacrylates, and copolymers and blends thereof. Preferably, if the microparticle is formed from a copolymer or blend of polymers, the copolymer or blend is formed from polymers with a high glass transition temperature or high melting point, and does not contain any polymer with a low glass transition temperature, i.e. a glass transition temperature lower than 60° C., or a melting point that is lower than 50° C.

Suitable polymers with a glass transition temperature greater than or equal to 60° C. or suitable polymers with a melting point greater than or equal to 50° C. include, but are not limited to, polyacrylates, polymethacrylates, polycarbonates, polypropylenes, polyalkylenes, polyalkylene glycols, polyalkylene oxides, polyalkylene terephthalates, polyvinyl ethers, polyvinyl halides, polysiloxanes, polyurethanes and copolymers thereof, hydroxyalkyl celluloses, cellulose ethers, nitro celluloses, methyl cellulose, ethyl cellulose, cellulose acetate, cellulose propionate, cellulose acetate butyrate, cellulose triacetate, cellulose sulphate sodium salt, poly(methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly(phenylmethacrylate), poly(methyl acrylate), poly(isopropyl acrylate), poly(isobutylacrylate), poly(octadecyl acrylate), polyethylene, poly(ethylene terephthalatepoly(vinyl acetate), and poly vinyl chloride polystyrene, and mixtures, copolymers, and blends thereof.

Preferred polymers include polyacrylates and polymethacrylates.

In certain embodiments, the polymethacrylate is poly(methyl methacrylate) (PMMA). Medical grade PMMA (MW=35 kDa; residual MMA monomer<0.1%) is commercially available from Vista Optics Ltd. (Widnes, UK).

B. Shapes and Sizes

The microparticles can have any shape. Typically the microparticles are spherical. Other suitable shapes include, but are not limited to, flakes, triangles, ovals, rods, polygons, needles, tubes, cubes and cuboid structures.

In certain embodiments, the microparticles have a diameter of less than 10, 9, 8, 7, 6, 5, 4, 3, 2, 1, 0.9, 0.8, 0.7, 0.6, 0.5, 0.4, 0.3, 0.2 or 0.1 micron(s). Any of these values may be used to define a range for the diameter of the microparticle. For example the diameter of the microparticle may be from about 0.1 to about 10 microns, from about 0.1 to about 1 micron, or from about 0.1 to about 2 microns. Typically, the microparticle diameter is less than 5 microns. Preferably for compositions that are used as additives in a tattoo ink, the microparticle diameter ranges from about 1 to about 10 microns, more preferably from about 1 to 2 microns. Microparticles with a diameter of 10 microns and less may be introduced into the skin via a tattoo gun or any similar device.

In other embodiments, larger microparticles or particles may be used. For example the microparticles may have a diameter of ranging from 10 microns to 1000 microns. In these embodiments, the microparticles may be delivered to the skin via an intradermal injection.

C. Loading of Encapsulated Personalizing Substance in Microparticles

Typically, the concentration of a personalizing substance encapsulated in a microparticle is presented as percent loading. Because values for the percent loading are dependent on the weights of the personalizing substances, percent loading values for the different personalizing substances may vary significantly. Therefore, different ranges for the percent loading for different personalizing substances are contemplated.

In some embodiments, low concentrations (e.g., up to 0.1% w/w or lower) of the personalizing substance in the microparticles are required to prevent leaching of the personalizing substance from the microparticle.

In some embodiments, such as when the encapsulating material is DNA, only a small sample is provided for encapsulation. In these embodiments, the microparticles typically contain low concentrations of DNA. However, if a large amount of the encapsulating material is provided, the loading of the encapsulating material in the microparticle can be higher as long as the resulting microparticles do not allow DNA to be released.

In some embodiments, the microparticle comprises about 0.00001, 0.00005, 0.0001, 0.0005, 0.001, 0.005, 0.01, 0.02, 0.03, 0.04, 0.05, 0.06, 0.07, 0.08, 0.09, 0.1, 0.5, 1, 2, 3, 4, 5, 6, 7, 8, 9 or 10% weight of the encapsulating material/weight of the microparticle (w/w). In some embodiments, the microparticles comprise less than about 0.00001, 0.00005, 0.0001, 0.0005, 0.001, 0.005, 0.01, 0.02, 0.03, 0.04, 0.05, 0.06, 0.07, 0.08, 0.09, 0.1, 0.5, 1, 2, 3, 4, 5, 6, 7, 8, 9 or 10% weight of the encapsulating material/weight of the microparticle (w/w). Any of these values may be used to define a range for the concentration of the encapsulating material in the microparticle. For example, the microparticles may contain encapsulating material in an amount ranging from about 0.00001 to about 10% w/w or from about 0.001 to about 2% w/w. In some embodiments, the amount of encapsulating material in the microparticles is less than about 0.1% w/w.

1. Percent Loading of DNA

Typically, percent loading for DNA in the microparticles ranges from 0.000001% to 0.1% weight of DNA to the total weight of the microparticles (% w/w). In preferred embodiments, the amount of DNA in the microparticles is less than 0.01% (w/w) DNA, more preferably the amount of DNA in the microparticles ranges from 0.001% to 0.00001% (w/w). These loading ranges are generally applicable to single-walled microparticles.

However, for embodiments, in which the microparticles are double walled microparticles, higher loadings of DNA may be used. It is expected that the structure of the double-walled microparticles protects the DNA from leaching out of the microparticles. In these embodiments, the amount of DNA in the microparticles may range from 0.000001% to about 5% weight of DNA to the total weight of the microparticles (% w/w), optionally from about 1%-5% (w/w).

2. Percent Loading of Other Personalizing Substances

Typically, the percent loading of personalizing substances other than DNA is higher than the loadings of DNA in the microparticles. For example, the amount of the personalizing substance in the microparticle may range from about 0.001 to about 10% w/w or from about 0.001 to about 2% w/w. Optionally, the amount of the personalizing substance in the microparticle is less than about 0.001, 0.005, 0.01, 0.02, 0.03, 0.04, 0.05, 0.06, 0.07, 0.08, 0.09, 0.1, 0.5, 1, 2, 3, 4, 5, 6, 7, 8, 9 or 10% w/w. Any of these values may be used to define a range for the concentration of the substance in the microparticle. For example, the amount of the personalizing substance in the microparticle may range from about 0.001 to about 10% w/w or from about 0.001 to about 2% w/w. In a particular embodiment, the microparticle comprises less than about 0.1% w/w of the personalizing substance other than DNA.

3. Carrier

In certain embodiments, the compositions described herein are formulated for injection into the skin of a human. For example, the composition may comprise a suitable biocompatible carrier for delivery to a human via injection. Suitable carriers include any alcohol, including but not limited to ethyl alcohol, isopropyl alcohol, or water. Suitable carriers also include any combination of alcohol and water. Typically the amount of alcohol in the carrier ranges from about 5% to about 30% (w/w), and the amount of water in the carrier ranges from about 40% to about 70% (w/w).

In preferred embodiments, the carrier is a solution of 60% water, 30% glycerin (glycerol), and 10% ethanol. Other carrier solutions including 55% water, 30% glycerin and 15% ethanol; 50% water, 30% glycerin, and 20% ethanol; 45% water, 30% glycerin, and 25% ethanol; or 40% water, 30% glycerin and 30% ethanol, are also contemplated.

4. Exemplary Composition Containing DNA

In certain embodiments, the personalizing substance to be delivered to the individual, contains DNA from a human, a non-human animal (e.g. a pet), or a plant.

In a particular embodiment, the DNA is from a human. No two people have the exact same sequence of DNA in their cells. The differences in the DNA in individual humans gives rise to the unique DNA profiles that can be used to distinguish individuals. In addition, the unique DNA profile of each individual provides a means for verifying that the personalizing substance is from a particular individual. Accordingly, incorporation of DNA into a carrier or into a tattoo ink provides a unique characteristic to the tattoo ink or carrier that may be verified, for example, through DNA sequencing or analysis of genetic markers.

The DNA may be coding or non-coding genomic DNA, coding or non-coding mitochondrial DNA or complementary DNA (cDNA). cDNA is synthesized from RNA using reverse transcriptase. The genomic DNA, mitochondrial DNA, and RNA for synthesis of cDNA may be isolated from any organism, including but not limited to humans, animals, and plants. In some embodiments, the DNA is isolated from a single organism, for example, a human. In other embodiments, the DNA is isolated from two or more organisms, for example, two or more humans. Methods of isolating genomic DNA, mitochondrial DNA and RNA, and methods of cDNA synthesis are well known in the art and are described, for example, in Sambrook, et al., Molecular Cloning. (4th ed.). Cold Spring Harbor, N.Y.: Cold Spring Harbor Laboratory.

D. DNA Isolation and Amplification

In some embodiments, the DNA contained in the personalizing substance is isolated directly from an organism, such as genomic DNA or mitochondrial DNA. In other embodiments, the DNA contained in the personalizing substance is amplified from a sample collected from the organism, for example by polymerase chain reaction (PCR). Multiple DNA segments for tetranucleotide PCR amplification typically may be amplified in a single tube. Such multiple amplification of several DNA regions is known in the art as multiplex PCR. The multiple PCR products are separated as known in the art, for example, by electrophoresis, and an instrument reads the electrophoresis gel or image to automatically analyze the sizes of the PCR products. In some embodiments, the DNA contained in the personalizing substance is cDNA reverse transcribed from RNA isolated from the organism, as mentioned above.

The DNA may be sequenced so that verification steps described below may be performed. (Sambrook, et al., Molecular Cloning. (4th ed.). Cold Spring Harbor, N.Y.: Cold Spring Harbor Laboratory).

Preparation of DNA samples for use as a personalizing substance may proceed as follows, although other methods of preparing analogous DNA samples are known to the skilled artisan. One preferred method includes the following general steps:

A sample for preparation of the DNA contained in the personalizing substance is collected from a sample of cheek swab, skin, hair, saliva, or blood or other tissue from an organism as is known in the art. A cheek swab sample is preferred. Protocols for collecting and handling the sample are known in the art.

For example, a DNA isolation kit suitable for isolating genomic DNA from buccal cells, may be used to isolate DNA from the cheek swab. These kits are commercially available and usually generate 0.5-2 micrograms of total DNA. Desirable genomic regions containing polymorphic genetic markers (such as STRs and SNPs) of the isolated DNA are then amplified via PCR to generate micrograms, typically from 1 to 10 micrograms, of DNA to be used as a personalizing substance. The amplified DNA may be sequenced so that verification steps described below may be performed. This amplified DNA is the personalizing substance that is encapsulated into microparticles.

Optionally, the encapsulation of personalizing DNA molecule may include a control DNA molecule of a known sequence that is included at the same amount as the personalizing DNA molecule. The control DNA may be used for testing to determine whether any of encapsulated DNA is released, such as via the in vitro method described above.

Alternatively, or optionally, the personalizing DNA may be partially or fully labeled with fluorophores, such as Alexa Fluor) dyes (Molecular Probes, Inc.). The labeled DNA may be used to confirm that the DNA was successfully encapsulated, such as with flow cytometry of the encapsulated particles. Alternatively or additionally, the labeled DNA may be used to determine whether any of the encapsulated DNA will be released following delivery to an individual's skin. This test may be performed by measuring the fluorescence of the aqueous solution, buffer, or supernatant in which empty microparticles or those encapsulating labeled DNA were tested for DNA release in an in vitro method, such as described above.

Transmission electron microscopy (TEM) may be used to verify encapsulation of the amplified DNA.

In some embodiments, genomic DNA, mitochondrial DNA, and/or RNA is isolated from the sample using methods known in the art, such as those described in Sambrook et al. (cited above). The concentration and integrity of the extracted DNA or RNA may be determined, for example, to inform the decision to proceed with PCR or reverse transcription or to obtain another sample.

In some embodiments, the DNA contained in the personalizing substance may be generated by PCR. For example, DNA comprising STRs may be amplified by PCR using primers that amplify three to five tetranucleotide repeat segments of the genomic DNA sample, optionally incorporating a detectable label, such as a radioactive or fluorescent label, as is known in the art. PCR primers for amplifying the DNA may be obtained from a commercial source or may be synthesized using methods known in the art. Software for design of PCR primers is well known in the art.

Examples of preferred STRs that may be amplified by PCR are set forth in Table 2 below. The skilled artisan will appreciate that additional suitable tetranucleotide and pentanucleotide repeats may also be amplified. One of the preferred qualities of suitable tetranucleotide DNA repeats is high heterozygosity (variability between individuals) in the subject population. Another preferred quality of suitable tetranucleotide DNA repeats is that they do not encode a biologically active product, for example, a protein, tRNA, rRNA, miRNA, or siRNA. A further preferred quality of suitable tetranucleotide DNA repeats is that they do not induce an immune response and produce no therapeutic action in the recipient.

TABLE 2

Preferred Repeats in DNA for amplification

| Human Marker | Allele Distribution (bp) | Number of Repeats |
|---|---|---|
| 3S1358 | 98 to 146 | 8 to 20 |
| 5S818 | 133 to 169 | 7 to 16 |
| 7S820 | 215 to 247 | 6 to 14 |
| 8S1179 | 163 to 213 | 7 to 19 |
| 13S317 | 161 to 205 | 5 to 16 |
| 16S539 | 133 to 173 | 5 to 15 |
| 21S11 | 201 to 257 | 24 to 38 |
| 8S1106 | 109 to 133 | 7 to 13 |
| 1S518 | 182 to 198 | 13 to 17 |
| 6S1017 | 354 to 374 | 10 to 15 |
| 17S1304 | 197 to 213 | 10 to 14 |
| 4S2408 | 336 to 360 | 13 to 19 |
| 5S1467 | 173 to 189 | 8 to 12 |
| 19S245 | 225 to 249 | 16 to 22 |

The resulting PCR products are typically analyzed, for example, by electrophoresis, for the successful generation of tetranucleotide repeats and to confirm that the sample shows relatively unique representation of a DNA sample from an individual.

E. Verification of Amplified DNA

In some embodiments, the DNA is analyzed to confirm that the DNA contained in the personalizing substance was obtained or generated from the desired source organism. For example, for DNA comprising STRs, the pattern of PCR products in the DNA contained in the personalizing substance may be compared to a control sample obtained from the source organism. The DNA contained in the personalizing substance may also be analyzed by DNA sequencing, for example cDNA sequencing or whole genome sequencing, to confirm that the DNA contained in the personalizing substance is from the desired source organism.

The sequencing of the DNA may be performed using methods known in the art. These include, but are not limited to basic sequencing methods, such as Sanger's method, Maxam-Gilbert sequencing and chain termination methods (Franga et al., *Quarterly Review of Biophysics*, 35(2):169-200, 2002), advanced methods and de novo sequencing, such as shotgun sequencing and bridge PCR (Braslavky et al., *Proc. Natl. Acad. Sci*, 100(7):3960-3964, 2003), or next-generation methods. Next-generation sequencing applies to genome sequencing, genome resequencing, transcriptome profiling (RNA-Seq), DNA-protein interactions (ChIP-sequencing), and epigenome characterization (de Magalhaes et al., *Ageing Res Rev.* 9(3)315-323, 2010; Liu et al., *Journal of Biomedicine and Biotechnology*, 2012:1-11, article ID 251364, 2012; and Hall, *The Journal of Experimental Biology*, 209:1518-1525, 2007). Resequencing is necessary, because the genome of a single individual of a species will not indicate all of the genome variations among other individuals of the same species.

Next Generation sequencing encompasses a number of methods, including, but not limited to single-molecule real-time sequencing, massively parallel signature sequencing, (MPSS), Polony sequencing, 454 pyrosequencing, ion torrent semiconductor sequencing, DNA nanoball sequencing, heliscope single molecule sequencing, sequencing by ligation (SOLID sequencing) and single molecule real time sequencing (SMRT). These methods are detailed and compared in Liu et al., *Journal of Biomedicine and Biotechnology*, 2012:1-11, article ID 251364, 2012, and Hall, *The Journal of Experimental Biology*, 209:1518-1525, 2007.

In some embodiments, the DNA contained in the personalizing substance is analyzed before the personalizing substance is combined with a carrier or in tattoo ink. In other embodiments, the DNA contained in the personalizing substance is analyzed after the personalizing substance is combined with a carrier or tattoo ink.

The DNA may be purified to obtain pharmaceutical/biologics grade DNA suitably free of contaminants.

II. Methods of Making the Compositions

The microparticles may be made using a variety of known microencapsulation methods, such as solvent evaporation, multi-walled (or double walled) microencapsulation, coacervation, and melt processing.

Any of the non-bioerodible, hydrophobic polymers discussed above may be used to form the polymeric microparticles.

1. Solvents

Solvents that may be used in forming the microparticles include organic solvents such as methylene chloride, which leave low levels of residue that are generally accepted as safe. Suitable water-insoluble solvents include methylene chloride, chloroform, dicholorethane, ethyl acetate and cyclohexane. Additional solvents include, but are not limited to, alcohols such as methanol (methyl alcohol), ethanol, (ethyl alcohol), 1-propanol (n-propyl alcohol), 2-propanol (isopropyl alcohol), 1-butanol (n-butyl alcohol), 2-butanol (sec-butyl alcohol), 2-methyl-1-propanol (isobutyl alcohol), 2-methyl-2-propanol (t-butyl alcohol), 1-pentanol (n-pentyl alcohol), 3-methyl-1-butanol (isopentyl alcohol), 2,2-dimethyl-1-propanol (neopentyl alcohol), cyclopentanol (cyclopentyl alcohol), 1-hexanol (n-hexanol), cyclohexanol (cyclohexyl alcohol), 1-heptanol (n-heptyl alcohol), 1-octanol (n-octyl alcohol), 1-nonanol (n-nonyl alcohol), 1-decanol (n-decyl alcohol), 2-propen-1-ol (allyl alcohol), phenylmethanol (benzyl alcohol), diphenylmethanol (diphenylcarbinol), triphenylmethanol (triphenylcarbinol), glycerin, phenol, 2-methoxyethanol, 2-ethoxyethanol, 3-ethoxy-1,2-propanediol, Di(ethylene glycol)methyl ether, 1,2-propanediol, 1,3-propanediol, 1,3-butanediol, 2,3-butanediol, 1,4-butanediol, 1,2-pentanediol, 1,3-pentanediol, 1,4-pentanediol, 1,5-pentanediol, 2,3-pentanediol, 2,4-pentanediol, 2,5-pentanediol, 3,4-pentanediol, 3,5-pentanediol, and combinations thereof. A preferred alcohol is isopropanol.

Materials that may be used to formulate a coacervate system comprise anionic, cationic, amphoteric, and non-ionic surfactants. Anionic surfactants include di-(2 ethylhexyl)sodium sulfosuccinate; non-ionic surfactants include the fatty acids and the esters thereof; surfactants in the amphoteric group include (1) substances classified as simple, conjugated and derived proteins such as the albumins, gelatins, and glycoproteins, and (2) substances contained within the phospholipid classification, for example lecithin. The amine salts and the quaternary ammonium salts within the cationic group also comprise useful surfactants. Other surfactant compounds useful to form coacervates include polysaccharides and their derivatives, the mucopolysaccharides and the polysorbates and their derivatives. Synthetic polymers that may be used as surfactants include compositions such as polyethylene glycol and polypropylene glycol. Further examples of suitable compounds that may be utilized to prepare coacervate systems include glycoproteins, glycolipids, galactose, gelatins, modified fluid gelatins and galacturonic acid.

3. Surfactants

Hydrophobic surfactants such as fatty acids and cholesterol may be added during preparation of the microparticles to improve the resulting distribution of hydrophobic personalizing substances in hydrophobic polymeric microparticles. Examples of suitable fatty acids include butyric acid, valeric acid, caproic acid, enanthic acid, caprylic acid, pelargonic acid, caprylic acid, undecylic acid, lauric acid, tridecylic acid, myristic acid, pentadecylic acid, palmitic acid, heptadecylic acid, stearic acid, nonadecanoic acid, arachic acid, isocrotonic acid, undecylenic acid, oleic acid, elaidic acid, sorbic acid, linoleic acid, linolenic acid and arachidonic acid.

Hydrophilic surfactants such as TWEEN® 20 and polyvinyl alcohol (PVA) improve distribution of hydrophilic dye in the polymers. Amphiphilic surfactants are preferred if the dye is hydrophilic and the polymer is hydrophobic.

Surfactant such as a fatty acid or a pharmacologically acceptable salt thereof is typically added in a ratio of from 0.2 to 1 part by weight of the fatty acid or salt thereof to 1 part by weight of the dye.

4. Micronizing and Nanoparticle Formation

Methods for micronizing the personalizing substance for production of nanoparticles, if needed, include, for example, sonication and/or production of shear forces, and rotor stator mixing or milling with a concentric shaft, at a speed between, for example, 5,000 RPM and 25,000 RPM.

In some embodiments where DNA is the personalizing substance, the DNA may be prepared by precipitation using standard techniques, such as ethanol or isopropanol precipitation, or salt precipitation. In some embodiments, the DNA is micronized by precipitation with calcium phosphate, and the precipitate is not dissolved but instead incorporated directly as nanoparticles into the microparticle. In some embodiments, the DNA is encapsulated as an emulsion in water which is later removed after the encapsulation process to produce a small solid particle of DNA. The DNA may also be bound to a solid nanoparticle such as silicon dioxide or gold, or crosslinked together to form aggregates.

Methods of encapsulating DNA in nanoparticles are described in the art. See, for example, US 2009/0311295, and van de Berg et al., 2010, Journal of Controlled Release 141: 234-240.

5. Distribution of Nanoparticles within Microparticles

Preferably the nanoparticle containing the personalizing substance are uniformly distributed within the polymer microparticle and at a low loading level to avoid any leaching of the encapsulated personalizing substance. This is particularly desirable when the encapsulating material is or contains DNA.

The problem with most methods of manufacture of microparticles is that while the nanoparticles are dispersed initially following addition to polymer solution, the nanoparticles rapidly settle towards the bottom. Then when solvent is removed, the nanoparticles are present more preferentially in one part of the polymer than another. It is difficult to keep the nanoparticles dispersed while at the same time removing the polymer solvent to form the microparticles. Therefore, methods have been developed wherein the nanoparticles are dispersed in the polymer solution so that the solution is "stabilized" so that the nanoparticles stay uniformly distributed within the polymer for a period of time sufficient to form the microparticles. This time may be as short as ten minutes or as long as a few hours. The amount of time that the nanoparticle will remain suspended in the polymer depends on the size and composition of the nanoparticle.

Stability is a function of the selection of the polymer, the solvent composition as well as the method of dispersion and the density of the encapsulated material. For example, the concentration of the organic polymeric solution must be adjusted to keep the nanoparticles dispersed and prevent settling of the nanoparticles during the process of encapsulation. In a method theoretically (if not mechanistically) analogous to beating egg whites, the polymer solution is sonicated or otherwise subjected to shear forces, using an open blade mixer or rotor stator at 5000-25,000 RPM, or milled using a concentric shaft, until stable. Alternatively or in addition, the solvent and surfactant, if present, can be used to alter the surface properties of the nanoparticles so that they remain suspended in the polymer solution. The solvent is then removed to form the microparticles having a uniform dispersion of nanoparticles within the polymer.

6. Methods of Making Microparticles

There are several processes whereby microparticles can be made, including, for example, multi-walled microencapsulation, hot melt encapsulation, phase separation encapsulation, spontaneous emulsion, solvent evaporation microencapsulation, solvent removal microencapsulation, and coacervation. These methods are known in the art. Detailed descriptions of the methods are discussed in Mathiowitz et al., "Microencapsulation", in Encyclopedia of Controlled Drug Delivery, vol. 2, pp. 495-546, 1999, John Wiley & Sons, Inc. New York, N.Y., and are concisely presented below. A preferred method is solvent evaporation microencapsulation (specifically high oil to aqueous phase ratio to achieve small particles with addition of surfactant such as oleic acid to improve dispersion of the personalized fragment in the polymeric phase phase). For solvent evaporation, the minimum concentration is 0.1% w/v (polyvinyl alcohol to water). Another preferred method includes addition of the nanoparticles into the polymer liquefied by melting to ensure uniform distribution.

The dispersion of the nanoparticles within the polymer matrix can be enhanced by varying: (1) the solvent or combination of solvents used to solvate the polymer; (2) the ratio of the polymer to the solvent; (3) the size of the nanoparticle to be encapsulated; and (4) the percentage of the nanoparticle relative to the polymer (i.e. nanoparticle loading). The dispersion of the nanoparticles within the polymer matrix may also be enhanced by using surfactants.

In certain embodiments, the personalizing substance is analyzed during the process of preparing the microparticles, e.g. after micronization and/or after encapsulation, to confirm the identity of the personalizing substance. Generally, the microparticles are prepared in small batches.

A. Hot Melt Microencapsulation

In hot melt microencapsulation, the personalizing substance (optionally in the form of nanoparticles) to be encapsulated is added to molten polymer. This mixture is suspended as molten droplets in a nonsolvent for the polymer (often oil-based) which has been heated to approximately 10° C. above the melting point of the polymer. The emulsion is maintained through vigorous stirring while the nonsolvent bath is quickly cooled below the glass transition of the polymer, causing the molten droplets to solidify and entrap the core material.

B. Phase Separation Microencapsulation

In phase separation microencapsulation the personalizing substance (optionally in the form of nanoparticles) to be encapsulated is dispersed in a polymer solution with stirring. While continually stirring to uniformly suspend the material, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the personalizing substance (optionally in the form of nanoparticles) in a droplet with an outer polymer shell.

C. Spontaneous Emulsification

Spontaneous emulsification involves solidifying emulsified liquid polymer droplets by changing temperature, evaporating solvent, or adding chemical cross-linking agents. The physical and chemical properties of the encapsulant, and the personalizing substance to be encapsulated, dictates the suitable methods of encapsulation. Factors such as hydrophobicity, molecular weight, chemical stability, and thermal stability affect encapsulation.

D. Melt-solvent Evaporation Method

In the melt-solvent evaporation method, the polymer is heated to a point of sufficient fluidity to allow ease of manipulation (for example, stirring with a spatula). The temperature required to do this is dependent on the intrinsic properties of the polymer. For example, for crystalline polymers, the temperature will be above the melting point of the polymer. After reaching the desired temperature, the personalizing substance (optionally in the form of nanoparticles) is added to the molten polymer and physically mixed while maintaining the temperature. The molten polymer and personalizing substance are mixed until the mixture reaches the maximum level of homogeneity for that particular system. The mixture is allowed to cool to room temperature and harden. This technique results in dispersion of the personalizing substance in the polymer.

High shear turbines may be used to stir the dispersion, complemented by gradual addition of the nanoparticle into the polymer solution until the desired loading is achieved. Alternatively the density of the polymer solution may be adjusted to prevent settling of the nanoparticle during stirring.

E. Solvent Evaporation Microencapsulation

In solvent evaporation microencapsulation, the polymer is typically dissolved in a water immiscible organic solvent and the personalizing substance (optionally in the form of nanoparticles) to be encapsulated is added to the polymer solution as a dispersion, suspension or emulsion in an organic solvent An emulsion (i.e. a second emulsion if the encapsulating material is added as an emulsion) is formed by adding this dispersion, suspension or emulsion to a beaker and vigorously stirring the system. Any suitable surface active agent may be used to stabilize the emulsion. Typical surface active agents include, but are not limited to polyethylene glycol or polyvinyl alcohol (PVA)). The organic solvent is evaporated while continuing to stir. Evaporation results in precipitation of the polymer, forming solid microcapsules containing core encapsulated material, where the encapsulated material is in the form of an emulsion or a solid.

The solvent evaporation process can be used to entrap a liquid core material in a polymer or in copolymer microcapsules, however the liquid is removed by conventional methods after the polymer has encapsulated the substance.

The solvent evaporation process is the preferred process for encapsulating DNA.

F. Solvent Removal Microencapsulation

In solvent removal microencapsulation, the polymer is typically dissolved in an oil miscible organic solvent and the personalizing substance (optionally in the form of nanoparticles) to be encapsulated is added to the polymer solution as a suspension or solution in organic solvent. Surface active agents can be added to improve the dispersion of the material to be encapsulated. An emulsion is formed by adding this suspension or solution to vigorously stirring oil, in which the oil is a nonsolvent for the polymer and the polymer/solvent solution is immiscible in the oil. The organic solvent is removed by diffusion into the oil phase while continuing to stir. Solvent removal results in precipitation of the polymer, forming solid microcapsules containing core material.

G. Coacervation

Encapsulation procedures for various substances using coacervation techniques have been described in the art, for example, in GB-B-929 406; GB-B-929 401; U.S. Pat. Nos. 3,266,987; 4,794,000 and 4,460,563. Coacervation is a process involving separation of colloidal solutions into two or more immiscible liquid layers (Ref. Dowben, R. General Physiology, Harper & Row, New York, 1969, pp. 142-143.). Through the process of coacervation, compositions comprised of two or more phases known as coacervates may be produced. The ingredients that comprise the two phase coacervate system are present in both phases; however, the colloid rich phase has a greater concentration of the components than the colloid poor phase.

In the coacervation process, the polymer or copolymer is dissolved in a miscible mixture of solvent and nonsolvent, at a nonsolvent concentration which is immediately below the concentration which would produce phase separation (i.e., cloud point). The liquid core material is added to the solution while agitating to form an emulsion and disperse the material as droplets. Solvent and nonsolvent are vaporized, with the solvent being vaporized at a faster rate, causing the polymer or copolymer to phase separate and migrate towards the surface of the core material droplets. This phase-separated solution is then transferred into an agitated volume of nonsolvent, causing any remaining dissolved polymer or copolymer to precipitate and extracting any residual solvent from the formed membrane. The result is a microcapsule composed of polymer or copolymer shell with a core of liquid material.

For example, DNA may be dissolved in water and then an emulsion of the dissolved DNA is formed in an organic polymeric solution. This emulsion is then added to aqueous solution and mixed (optionally, for DNA having lengths of less than 2 kilobases (kb) high shear may be used) until the organic solvent evaporates, and then the entire mixture is washed and frozen and lyophilized, resulting in a dry particle of DNA inside the polymer.

The material can be encapsulated using an emulsifier such as Tween 80®, oleic acid, lecithin, Brij®92, Span®80, Arlacel® 83, and Span® 85. Alternatively, the material can be encapsulated without the use of an emulsifier.

H. Multi-walled Microencapsulation

Multiwall polymer microspheres may be prepared by dissolving two polymers in a solvent. A personalizing substance to be incorporated is dispersed in the polymer solution, and the mixture is suspended in a continuous phase. The solvent then is slowly evaporated, creating microspheres with an inner core formed by one polymer and an outer layer of the second polymer. The continuous phase can be either an organic oil, a volatile organic solvent, or an aqueous solution containing a third polymer that is not soluble with the first mixture of polymers and which will cause phase separation of the first two polymers as the mixture is stirred.

Any two or more different non-biodegradable, hydrophobic polymers which are not soluble in each other at a particular concentration as dictated by their phase diagrams may be used. The multilayer microcapsules have uniformly dimensioned layers of polymer and can incorporate a range of substances.

For the preparation of double walled microspheres, each polymer is dissolved in a suitable solvent for that polymer, in separate containers, and mixed with surfactant such as oleic acid; the personalizing substance, optionally in the form of nanoparticles, is added to one of the polymeric solutions. Then the two (or more) polymeric solutions are mixed, and the mixture is then added to a large volume aqueous phase containing a surfactant, such as PVA, to form an emulsion (aqueous solution of water and some surfactant). High shear is applied. The oil to water phase ratio is typically 1:20 to ensure small microparticle sizes in the range of 1-5 microns, or even smaller microparticles, such as in the range of 1 to 2 microns.

Microspheres containing a polymeric core made of a first polymer and a uniform coating of a second polymer, and a substance incorporated into at least one of the polymers, can be made as described in U.S. Pat. No. 4,861,627.

I. Solvent Evaporation is Advantageous for Nanoparticle Microencapsulation

Solvent evaporation microencapsulation can result in the stabilization of the nanoparticle in a polymeric solution for a period of time sufficient for encapsulation of the nanoparticle. In certain embodiments, the nanoparticle is stabilized in the polymeric solution for about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes. In certain embodiments, the nanoparticle is stabilized in the polymeric solution for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes. In certain embodiments, the nanoparticle is stabilized in the polymeric solution for less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes. Any of these values may be used to define a range for the amount of time that the nanoparticle is stabilized in the polymeric solution. For example, the nanoparticle may be stabilized in the polymeric solution for about 10 minutes to about 30 minutes.

Stabilizing a personalizing substance within the dispersed phase (typically a volatile organic solvent) can be useful for most methods of microencapsulation that are dependent on a dispersed phase, including film casting, solvent evaporation, solvent removal, spray drying, phase inversion, and many others.

By stabilizing suspended nanoparticles within the dispersed phase, the nanoparticles remain homogeneously dispersed throughout the polymeric solution as well as the resulting polymer matrix that forms during the process of microencapsulation.

Solvent evaporation microencapsulation has several advantages. For example, solvent evaporation microencapsulation allows for the determination of the best polymer-solvent-nanoparticle mixture that will aid in the formation of a homogeneous suspension that can be used to encapsulate the nanoparticle. Solvent evaporation microencapsulation stabilizes the nanoparticles within the polymeric solution. This stabilization of nanoparticles is an advantage during small scale operation because one will be able to let suspensions of insoluble particles sit for short periods of time, making the process more secure and avoiding mixing between clients. Solvent evaporation microencapsulation allows for the creation of microparticles that have no release of the encapsulated material. Solvent evaporation microencapsulation avoids the problem of "burst effect", i.e. release of the encapsulated material within 1 hour of administration, which occurs with other encapsulation methods by allowing very low loading of the nanoparticles or personalizing substance and creating microparticles that have minimal pores.

7. Small Batch Preparation

In some embodiments, the compositions are made in small batches. The size of the batches may be limited by the nature and the amount of the personalizing substance, or by the number of end users.

In preferred embodiments, the personalizing substances are encapsulated into polymeric microparticles for personal use by one or few individuals. It is preferred, therefore, to prepare small batches of polymeric microparticles encapsulating the personalizing substance. In some embodiments, the prepared batch size may be as small as for single use by a single individual. In other embodiments, the prepared batch size may be as small as for single use by few, such as no more than two, no more than three, no more than four, no more than five, no more than six, no more than seven, no more than eight, no more than nine, or no more than ten individuals. In other embodiments, the batch size may be as small as for multiple uses by the same individual.

In other embodiments, the size of a small batch preparation may be guided by the amount of the available personalizing substance. For example, if DNA is used as a personalizing substance, the amount of DNA obtained from one individual through a cheek swab may only be small enough to produce a batch for single use by a single recipient. In a preferred embodiment, a single small batch yields a sufficient amount of microparticles encapsulating the personalizing substance for a single use by one end user.

In preferred embodiments, a small batch preparation process yields approximately 1-10 g of microparticles encapsulating the personalizing substance, in dry form, preferably about 1-2 g of microparticles encapsulating the personalizing substance, in dry form. For example, in some embodiments, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 6.0, 7.0, 8.0, 9.0 or 10 grams of the microparticle is prepared. In some embodiments, less than 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 6.0, 7.0, 8.0, 9.0 or 10 grams of the microparticle is prepared. Any of these values may be used to define a range of amounts in which the microparticle is prepared. For example, from 0.5 to 5 grams, or from 2 to 5 grams of the microparticle may be prepared. In a particular embodiment, approximately 2 grams of the microparticles is prepared.

IV. Methods of Use

The compositions described herein may be used on their own, in combination with a carrier, or as additives to substances, such as additives to tattoo ink, for delivery to the skin, typically via injection.

1. Use as Compositions

In some embodiments, the compositions described herein are suitable for use as compositions of personal significance. The use of the composition may be chosen by the end user. For example, the compositions may be used by the end user to preserve a substance of personal significance for a long period of time. The end user may store the composition, or chose to present the composition as a gift to another individual. Alternatively, the end user may choose to use the composition as an additive to other substance.

In some embodiments, the compositions are administered via injection at a desired skin site of an individual. Typically, the site contains a marking or a marking is added to the site to indicate the presence of the encapsulated personalizing substance in that location.

2. Use as Additives

In certain embodiments, the personalizing substances may be used as an additive to tattoo inks. The additives may be used to create a type of tattoo having a physical connection with a person or place or event.

Obtaining a personalized ink tattoo creates a physical connection with a person, object, place or event, because the personalized tattoo incorporates into the tattoo ink and, therefore, the image displayed in the skin, a personalizing substance.

Commercially available tattoo ink pigment typically is a composition in the form of a powder, often comprising heavy metal salts for pigmentation. The tattoo ink pigment is dissolved in a carrier, preferably alcohol or water, for injection into the skin and to distribute the pigment within the dermis. Alcohol also may impart an antimicrobial effect. Pre-dispersed inks containing the pigment pre-mixed with the carrier also are commercially available.

In certain embodiments, the microencapsulated personalizing substance is formulated in a dry powder form suitable for mixing with a carrier by the tattooist. In some embodiments, the microencapsulated personalizing substance may be mixed with a carrier and supplied as a pre-dispersed solution. The tattoo ink used in combination with the personalizing substance may be of any desired color known in the art.

In some embodiments, a tattoo ink comprising a personalizing substance may be prepared by mixing microparticles that contain a personalizing substance with a tattoo ink that is suspended in a liquid such as water, glycerin or witch hazel. The microparticles and tattoo ink may be mixed by shaking, stirring, vortexing, or light sonicating of the microparticles with the tattoo ink. In some embodiments, the concentration of the microparticles in the mixture of microparticles and tattoo ink is 0.001%, 0.005%, 0.01%, 0.05%, 0.1%, 0.5%, 1%, 2%, 3%, 4%, 5%, 6%, 7%, 8%, 9% or 10% w/w.

Once the microparticles that contain the personalizing substance are suspended within the tattoo ink, the tattoo ink may be administered to an individual by pouring a small amount (for example, less than 10 grams) of the microsphere-decorative tattoo ink slurry into a cup or other receptacle that is of sufficient size for one to dip a tattoo instrument that contains a tattoo needle or set of needles into the cup or receptacle. A tattoo may be created by dipping the tattoo needle into the cup or receptacle that contains the microparticle-tattoo ink mixture, and then piercing the skin with the needle to inject the microparticle-tattoo ink mixture into the skin.

The personalizing substance must be non-immunogenic in the recipient when applied to the skin. In some embodiments, the personalizing substance is encapsulated in a nanoparticle and/or microparticle before it is incorporated into the tattoo ink to prevent an immune response in the recipient.

V. Kits

Kits for obtaining a personalizing substance from an end user and kits for delivering the encapsulated personalizing substance to the end user are provided. A flow chart depicting the end-to-end process of obtaining the personalizing substance, and then isolating, preparing and delivering the encapsulated personalizing substance to the end user is presented in FIG. 2. A similar flow chart with DNA used as an exemplary personalizing substance is presented in FIG. 1.

In the process illustrated in FIG. 1, a cheek swab kit is provided to a customer. The customer uses the cheek swab to obtain a sample from the human or non-human animal of interest to the customer. Then the customer mails or otherwise delivers the sample to a lab. The lab isolates, amplifies (if needed), and purifies (if needed) the DNA, and then encapsulates the DNA in microparticles. Then the encapsulated DNA is lyophilized into a powder. Optionally, the powder is added to a carrier suitable for injection (not shown). Then the powder or solution is delivered to the customer. The customer then delivers the solution or powder to a tattoo shop, which either injects it in a desired site in the customer or adds it to tattoo ink and creates a tattoo on the customer.

Figure 2:
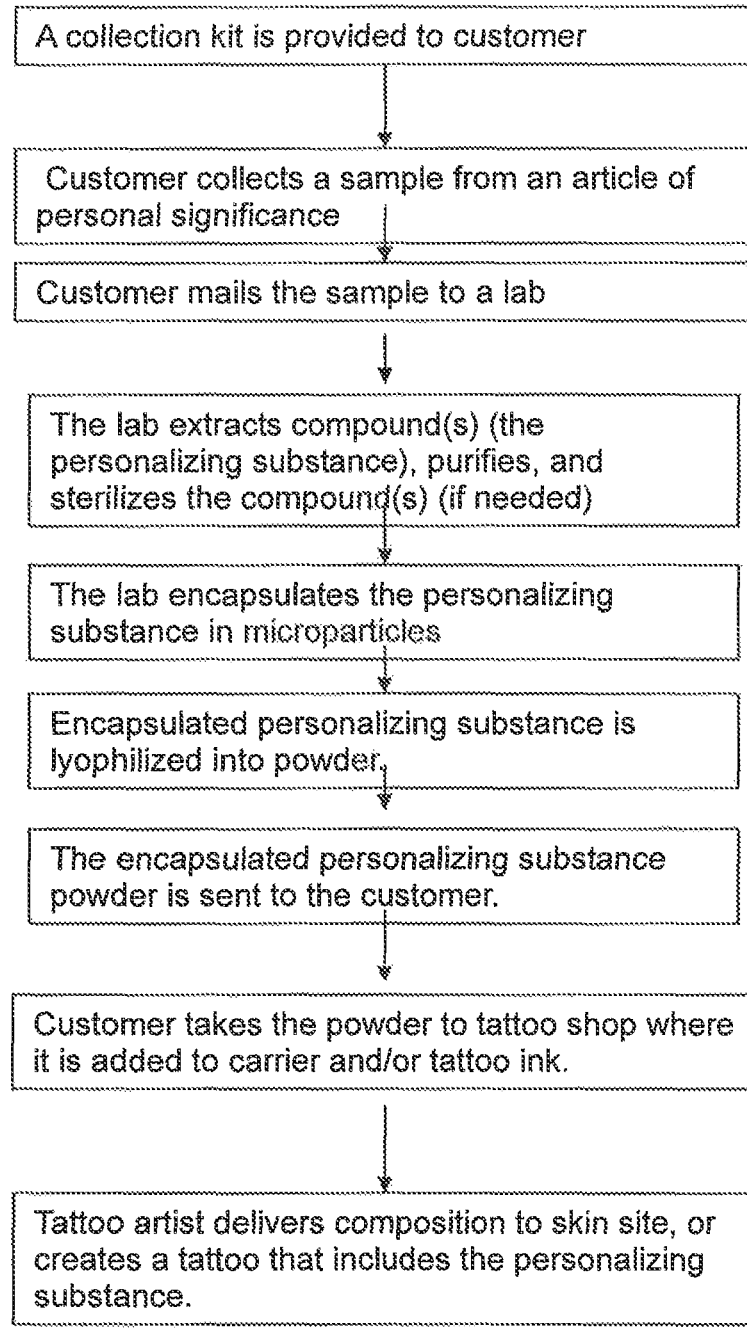
FIG. 2 is a flow chart showing the steps of an exemplary end-to-end process for delivering to a customer a tattoo that incorporates one or more compounds of personal significance. The steps performed by the customer and then by the lab generate compound(s) of personal significance, alone (dry powder), or in liquid form (e.g. with a carrier solution), which is added as an additive to a tattoo ink.

In the process illustrated in FIG. 2, a collection kit is provided to a customer. The customer places in the collection vessel (e.g. a vial) a sample from a source of interest to the customer. Then the customer mails or otherwise delivers the sample to a lab. The lab extracts, optionally purifies and/or sterilizes one or more compounds from the personalizing substance, and then encapsulates the personalizing substance in microparticles. Then the encapsulated personalizing substance is lyophilized into a powder. Optionally, the powder is added to a carrier suitable for injection (not shown). Then the powder or solution is delivered to the customer. The customer then delivers the solution or powder to a tattoo shop, which either injects it in a desired site in the customer or adds it to tattoo ink and creates a tattoo on the customer.

In some embodiments, the kits provide the equipment for obtaining a sample of the personalizing substance. The equipment may be tailored to the nature of the personalizing substance that will be provided. For example, if the personalizing substance is DNA, then the kit may include a foam or cotton-tipped cheek swab, a protective container for the swab, and instructions for use. If the personalizing substance is sand, then the kit may include a waterproof container and instructions for use.

In other embodiments, the kits provide the final product for use by the end user. In these embodiments, the kits may include a personalized substance, a carrier, and instructions for use. The kits may be customized to the preference of the end user. For example, the kits contain the personalizing substance in a powder form and a carrier.

In other embodiments, the kits may contain the personalizing substance pre-mixed with the carrier.

The kits may be delivered to the end user. Alternatively, the kits may be delivered to a tattoo shop where the kit components may be used by the end user at the tattoo shop.

EXAMPLES

Materials

Medical grade PMMA (Mw=35 kDa; residual MMA monomer<0.1%) was purchased from Vista Optics Ltd. (Widnes, UK), PVA (Mw=25 kDa; 88% hydrolyzed) was purchased from Polysciences, Inc. (Warrington, Pa., USA). dichloromethane (DCM; Burdick and Jackson, Muskegon, Mich., USA), ethyl acetate (EA; Mallinckrodt, Hazelwood, Mo., USA), and 1-octanol (Sigma-Aldrich, St. Louis, Mo., USA) were analytical grade solvents. Particles were made by solvent evaporation microencapsulation.

Example 1

Preparation of Blank poly(methyl methacrylate) (PMMA) Microparticles

Materials and Methods 500 mg of PMMA (about 25,000 MW) was weighed in a 20-ml glass scintillation vial; 15 ml of dichloromethane (DCM) was added to PMMA, vortexed for 30 seconds and sonicated for 5 minutes until solution became clear (1). At this point, the polymer was completely dissolved and there was no particulate matter.

250 ml of surfactant, 1.0% poly(vinyl alcohol) (PVA) (MW=25,000 Da; 88% hydrolyzed) was poured into a 1-L Virtis® flask (2).

100 ml of 0.5% PVA (MW=25,000 Da; 88% hydrolyzed) was poured into an 800 ml beaker (3). The beaker was placed under impeller (approximately 0.5 cm from bottom of beaker) with a speed set at 3,000 RPM.

Virtis® Cyclone was set to "55" (13,750 RPM); then 100 microliters of 1-octanol was added to the 1.0% PVA solution (2) and allowed to sit for 5 minutes (4). The PMMA solution (1) was added to (4) in the 1-L Virtis® flask. This mixture was mixed on the Cyclone for 15 minutes at 13,750 rpm.

The content was poured from the Virtis® flask into the 800 ml beaker containing 0.5% PVA (3) and stirred for about 24 hours to form a slurry of particles.

The slurry of particles was poured into 50 ml Eppendorf® tubes, the caps were screwed on and centrifuged for 20 minutes at 4,000 RPM (3345×g). PVA solution was aspirated off using a 50 ml pipette tip; this solution was kept for further evaluation. 40 ml of distilled water was added to tubes; mixed and shaken well until particles were resuspended in distilled water. The caps were screwed back on and centrifuged for an additional 20 minutes at 4,500 RPM. Distilled water was aspirated off using a 50 ml pipette tip. 40 ml distilled water was added to the tubes, mixed and shaken well until particles resuspended in distilled water. The caps were screwed back on and centrifuged for an additional 20 minutes at 4,000 RPM (3345×g). Distilled water was aspirated off using a 50 ml pipette tip. The slurry of particles was combined into one or two tubes, flash frozen and lyophilized for 48-72 hours.

Variation: The steps recited above were repeated with a different mass of PMMA (about 1M MW). The only difference occurred in the formation of the PMMA solution.

In the variation of Example 1, 500 mg of PMMA was weighed (about 1M MW) in a 50-ml Falcon tube; 30 ml of dichloromethane (DCM) was added to PMMA, vortexed (30 seconds) and sonicated (5 minutes) until the solution became clear.

Results

About 80% of PMMA used in this method formed blank PMMA microparticles.

Substantially the same yield was obtained in the variation of Example 1.

Example 2

Preparation of poly(methyl methacrylate) (PMMA) Microparticles Containing Low Loading of DNA and a Tattoo Ink Comprising the PMMA Microparticles Materials and Methods 1000 mg of PMMA (25,000 MW) was weighed in a 40-ml glass scintillation vial (1). DNA amplified at a mitochondrial locus was prepared. DNA was extracted from harvested human buccal mucosal cells by boiling for 10 minutes in the presence of 10% Chelex resin. A portion of the extracted DNA was PCR amplified using the following primers specific to a noncoding region of the human mitochondrial genome (bases 15,971-16411):

(SEQ ID NO: 1)
5'-TTAACTCCACCATTAGCACC-3'

(SEQ ID NO: 2)
5'-GAGGATGGTGGTCAAGGGAC-3'

The PCR product was purified using the Invitrogen PureLink Quick Gel Extraction & PCR Purification Combo kit. A portion of the purified DNA was labeled with AlexaFluor 488, ethanol precipitated to remove excess label, resuspended in water, and mixed with the remaining DNA to produce a solution suitable for encapsulation containing 5.6 nanograms of DNA per microliter. The DNA was dissolved in water, and the concentration of the solution was 5 micrograms per mL (2). About 100 microliters of DNA solution, corresponding to 0.56 microgram, was taken for microparticle preparation.

30 ml of dichloromethane (DCM) was added to the PMMA vial (1). 10 microliters of Span® 80 (sorbitan monooleate) was added to the PMMA solution and bath sonicated for 15 minutes (3). DNA (2) was pipetted into the PMMA solution (3) and mixed at 10,000 rpm for 1 minute to form an emulsion (4).

250 ml of surfactant, 1.0% PVA (MW≈25,000 Da; 88% hydrolyzed), was poured into a 1-L Virtis® flask. Virtis® Cyclone was set to 10000 RPM. 250 microliters of 1-octanol was added to the 1% PVA, mixed for 1 minute and then let to set for 5 minutes (5).

The PMMA-DNA emulsion (4) was added into the 1.0% PVA solution (5) and mixed for 15 minutes at 7,000 rpm (6).

200 ml of 0.5% PVA (MW≈25,000 Da; 88% hydrolyzed) was poured into an 800 ml beaker. The beaker was placed under impeller (approximately 0.5 cm from bottom of beaker) and the impeller speed was set at 3,000 RPM.

The contents from Virtis® flask (6) were poured into the 800 ml beaker containing 0.5% PVA and stirred for approximately 24 hours to form a slurry of particles.

The slurry of particles was poured into 50 ml Eppendorf® tubes, the caps were screwed on and centrifuged for 20 minutes at 4,000 RPM (3345×g). The PVA solution was aspirated off using a 50 ml pipette tip. This solution was kept for further evaluation. 40 ml of distilled water was added to tubes; mixed and shaken well, until particles resuspended in distilled water. Sonication was used, as needed, to break up any particle aggregates stuck to the bottom of the tubes. The caps were screwed back on and centrifuged for an additional 20 minutes at 4,500 RPM. Distilled water was aspirated off using a 50 ml pipette tip. 40 ml distilled water was added to tubes, mixed and shaken well, until particles resuspended in distilled water. The caps were screwed back on and centrifuged for an additional 20 minutes at 4,000 RPM (3345×g). The distilled water was aspirated off using a 50 ml pipette tip. The slurry of particles was combined into one or two tubes, flash frozen and lyophilized for 48-72 hours.

Results

About 60% of PMMA used in this method formed PMMA microparticles with low amounts of DNA.

The morphology of the particles was observed using scanning electron microscopy (SEM). In general, the particles were spherical in shape and had a smooth surface morphology. No pores were visible, even at high magnification (4,000×). The microspheres generally had a particle diameter of 1-2 micrometers. No fragments of polymer or DNA were observed in the micrographs. Observation of these microparticles under a fluorescent microscope revealed that a portion of them contained DNA labeled with AlexaFluor 488.

Tattoo ink containing a personalizing substance was prepared by mixing 1 g of the PMMA microparticles containing DNA described above with 19 g of decorative black tattoo ink, and shaking the mixture by hand. The decorative black tattoo ink comprised approximately 70% (w/w) of a liquid mixture (water, glycerin, and witch hazel) and approximately 30% (w/w) D&C Black No. 2 carbon black pigment.

We claim:

1. A method of applying an ink tattoo to the skin of an individual comprising
   injecting into the individual's skin a composition comprising:
   (i) tattoo ink; and
   (ii) non-bioerodible microparticles comprising DNA encapsulated in a biocompatible, hydrophobic, non-bioerodible polymer, wherein
   (a) the microparticles do not release a detectable amount of the DNA for at least one year after delivery to an individual's skin;
   (b) the DNA remains at the site of delivery; and
   (c) the microparticles comprise up to 0.01% (w/w) DNA.

2. The method of claim 1, wherein the injection is made at the site of an existing tattoo.

3. The method of claim 1, further comprising mixing the microparticles with the tattoo ink prior to injection.

4. The method of claim 1, wherein the step of injecting is repeated multiple times at different sites on the skin to form a tattoo design.

5. The method of claim 1, wherein the DNA is in the form of nanoparticles.

6. The method of claim 1, wherein the microparticles have a size ranging from 1 micron to 5 microns.

7. The method of claim 1, wherein the DNA comprises a personal identification characteristic selected from the group consisting of short tandem repeats (STRs), single nucleotide polymorphisms (SNPs), epigenetic markers, and methylated DNA.

8. The method of claim 1, wherein the polymer has a glass transition temperature that is greater than or equal to 60° C. or has a melting point greater than or equal to 50° C.

9. The method of claim 1, wherein the microparticles do not comprise visible pores using scanning electron microscopy (SEM).

10. The method of claim 1, wherein the microparticles do not comprise silica.

11. The method of claim 1, wherein the DNA is isolated from an organism.

12. The method of claim 11, wherein the organism is a human.

13. The method of claim 1, wherein the composition further comprises a carrier suitable for injection into the skin.

14. The method of claim 13, wherein the carrier is selected from the group consisting of ethyl alcohol, isopropyl alcohol, glycerol, and water.

15. The method of claim 13, wherein the carrier is a solution of 60% water, 30% glycerol, and 10% ethanol.

16. The method of claim 1, wherein the polymer is selected from the group consisting of polyvinyl acetate, polyacrylate, polymethacrylate, and copolymers and blends thereof.

\* \* \* \* \*